United States Patent [19]

Takayama et al.

[11] Patent Number: 5,013,656

[45] Date of Patent: May 7, 1991

[54] PROCESS FOR PRODUCING OROTIC ACID BY FERMENTATION

[75] Inventors: Kenichiro Takayama, Atsugi; Tomoko Matsunaga, Machida, both of Japan

[73] Assignee: Kyowa Hakko Kogyo Co., Ltd., Tokyo, Japan

[21] Appl. No.: 256,458

[22] Filed: Oct. 12, 1988

[30] Foreign Application Priority Data

Oct. 19, 1987 [JP] Japan .................. 62-261775

[51] Int. Cl.$^5$ .................. C12P 17/12; C12N 1/20
[52] U.S. Cl. .................. 435/122; 435/252.1; 435/843; 435/861
[58] Field of Search .................. 435/122, 136, 252.1, 435/172.1, 843, 861

[56] References Cited

U.S. PATENT DOCUMENTS 3,086,917  4/1963  Kinoshita et al. .................. 435/122

OTHER PUBLICATIONS

Chemical Abstracts, vol. 84, No. 17, Apr. 26, 1976, p. 400, Abstract No. 119951k, Columbus, Ohio, US.
Chemical Abstracts, vol. 73, No. 13, Sep. 28, 1970, p. 220, Abstract No. 65038v, Columbus, Ohio, US.
Herrmann et al., "Amino Acids Biosynthesis and Genetic Regulation", 1983, pp. 415-418, Addison-Wesley.
Stanbury et al., "Principles of Fermentation Technology", 1984, pp. 43-47.
Ozaki et al., "Amino Acid-Nucleic Acid", pp. 24-30, vol. 26, 1972.
Ogata et al., Microbial Production of Nucleic Acid Related Substances, John Wiley, 1976.

Primary Examiner—Douglas W. Robinson
Assistant Examiner—Irene Marx
Attorney, Agent, or Firm—Antonelli, Terry, Stout & Kraus

[57] ABSTRACT

A process is disclosed for producing orotic acid, the process involves culturing in a medium a microorganism of the genus Corynebacterium which is capable of producing orotic acid and has resistance to a pyrimidine analogue or to both a pyrimidine analogue and a sulfa drug, until orotic acid is accumulated in the culture, and recovering orotic acid therefrom.

2 Claims, No Drawings

PROCESS FOR PRODUCING OROTIC ACID BY FERMENTATION

BACKGROUND OF THE INVENTION

The present invention relates to a process for producing orotic acid by fermentation.

Orotic acid is a precursor of pyrimidine compounds which are structural components of nucleic acids, and is useful as a hepatic drug and as a starting material for synthesizing pyrimidine compounds such as uracil, cytosine and thymine.

Heretofore, uracil-requiring mutants of various microorganisms which accumulate orotic acid have been known ["Microbial Production of Nucleic Acid-Related Substances" p.184-191, edited by Association of Amino Acid and Nucleic Acid, Kodansha (1976)].

As to a microorganism belonging to the genus Corynebacterium, a process for producing orotic acid using Corynebacterium glutamicum (formerly designated Micrococcus glutamicus) which requires uracil has been known (Japanese Published Examined Patent Application No. 9950/63).

However, the known processes are still insufficient in efficiency of the production of orotic acid.

It is therefore an object of the present invention to provide a process for producing orotic acid in higher yield and at low cost.

SUMMARY OF THE INVENTION

According to the present invention, orotic acid can be produced in high yield by using a microorganism of the genus Corynebacterium which is capable of producing orotic acid and has resistance to a pyrimidine analogue or to both a pyrimidine analogue and a sulfa drug.

DETAILED DESCRIPTION OF THE INVENTION

In the present invention, any microorganism belonging to the genus Corynebacterium can be used, provided that it is capable of producing orotic acid and has resistance to a pyrimidine analogue or to both a pyrimidine analogue and a sulfa drug.

Examples of the pyrimidine analogue are 5-fluorouracil, 6-azauracil, 2-thiouracil, 5-hydroxyuracil and trimethoprim, and examples of the sulfa drug are sulfaguanidine, sulfathiazole, sulfapyridine and sulfamerazine.

As examples of the suitable strains, Corynebacterium glutamicum T-26 (FERM BP-1487) (resistant to 5-fluorouracil) (hereinafter referred to as T-26), Corynebacterium glutamicum T-29 (FERM BP-1488) (resistant to 5-fluorouracil and trimethoprim) (hereinafter referred to as T-29) and Corynebacterium glutamicum T-30 (FERM BP-1489) (resistant to 5-fluorouracil and sulfaguanidine) hereinafter referred to as T-30) may be mentioned. These strains have been deposited with the Fermentation Research Institute, Agency of Industrial Science and Technology, Ibaraki-ken, Japan.

A method for obtaining the above-mentioned suitable strains is explained below.

Corynebacterium glutamicum ATCC 14275 (uracil-requring) (hereinafter referred to as ATCC 14275) was cultured in a glucose-yeast extract-bouillon medium (1.0% glucose, 0.5% yeast extract, 1.0% peptone, 0.7% meat extract and 0.3% sodium chloride, pH 7.2) at 30° C. for 16 hours. After being cultured further in the same culture medium at 30° C. for 4 hours, the cells were collected, washed and suspended in an M/20 trismaleate buffer (pH 6.0) to make a cell suspension having a cell concentration of $10^8$/ml. To this suspension was added 250 μg/ml N-methyl-N'-nitro-N-nitrosoguanidine, and the suspension was maintained at 30° C. for 20 minutes. The cells were collected by centrifugation and washed well with an M/20 tris-maleate buffer. The cells were then smeared on a 5-fluorouracil-containing minimal medium plate having the following composition, and cultured at 30° C. for 4 days.

| Composition of the medium: | |
|---|---|
| 5-Fluorouracil | 100 μg/ml |
| Glucose | 1.0% |
| Ammonium sulfate | 0.1% |
| Urea | 0.1% |
| Dipotassium hydrogenphosphate | 0.1% |
| Magnesium sulfate | 0.04% |
| Sodium chloride | 0.02% |
| Ferrous sulfate | 0.001% |
| Manganese sulfate | 0.001% |
| Uracil | 20 mg/l |
| Biotin | 50 μg/l |
| Thiamine | 200 μg/l |
| (pH 7.0) | |

Cells in the colonies formed on the medium were inoculated on a glucose-yeast extract-bouillon slant, and then incubated in an Erlenmeyer flask for screening. T-26 was selected as a strain which is excellent in orotic acid productivity. Drug resistance of the strain is shown in Table 1. The same procedure as above was repeated except that T-26 was used as the parent strain and a minimal medium containing 100 μg/ml trimethoprim or 500 μg/ml sulfaguanidine instead of 100 μg/ml 5-fluorouracil was used. As a result, a trimethoprim-resistant strain, T-29, and a sulfaguanidine-resistant strain, T-30, were selected. Drug resistance of the strains is shown in Table 1.

TABLE 1

| Drug | Strain | | | |
|---|---|---|---|---|
| | ATCC 14275 | T-26 | T-29 | T-30 |
| 5-Fluorouracil (100 μg/ml) | − | + | + | + |
| Trimethoprim (100 μg/ml) | − | − | + | − |
| Sulfaguanidine (500 μg/ml) | − | − | − | + |

[Notes]
+: Growable; −: Not Growable

For the culturing of orotic acid-producing strains in the present invention, either a synthetic medium or a natural medium can be used so long as it contains carbon sources, nitrogen sources, inorganic salts, uracil, uracil-containing substances, and the like.

As the carbon sources, glucose, sucrose, maltose, blackstrap molasses, starch sugars, cellulose sugars, etc. may be used. As the nitrogen sources, ammonia, ammonium salts such as ammonium sulfate, ammonium chloride, ammonium nitrate, ammonium phosphate and ammonium carbonate, urea, and natural nitrogen sources such as peptone, meat extract, yeast extract, corn steep liquor, soybean meal and casein hydrolyzate, etc. may be used. As the inorganic salts, potassium dihydrogenphosphate, dipotassium hydrogenphosphate, magnesium sulfate, ferrous sulfate, manganese sulfate, sodium chloride, calcium chloride, etc. may be used. In cases where a uracil-requiring microorganism is used, uracil or a uracil-containing substance must be added to the medium in an appropriate amount (30 to 200 mg/l as uracil). As the uracil-containing substance, uridine, yeast extract, yeast cells, ribonucleic acids, etc. may be used.

Trace amounts of vitamins such as biotin, thiamine, nicotinic acid and pantothenic acid may also be used.

Culturing is carried out under aerobic conditions, e.g., by shaking culture or by submerged culture with aeration and agitation at a temperature of 25° to 37° C., preferably 28° to 34° C., and at a pH of 5 to 9, preferably 6.0 to 7.5, for 2 to 5 days.

As a neutralizer, calcium carbonate, aqueous ammonia, sodium hydroxide, potassium hydroxide, sodium carbonate, etc. may be used.

Orotic acid can be separated and recovered from the culture, for example, by heating the culture to 8020 –100° C. to dissolve orotic acid deposited and filtering the heated culture to remove cells, followed by the concentration and cooling of the filtrate to give crude crystals of orotic acid.

Certain embodiments of the invention are illustrated in the following examples.

EXAMPLE 1

T-26 was inoculated into a large test tube containing 10 ml of a seed culture medium having the composition shown below, and cultured at 30° C. for 24 hours. One milliliter of the seed culture was inoculated into a 300 ml-Erlenmeyer flask containing 20 ml of a production medium having the composition shown below, and cultured at 30° C. for 3 or 5 days. The results are shown in Table 2.

As a control, ATCC 14275 was cultured in the same manner as above. The results are shown in Table 2.

| Seed Culture Medium | |
|---|---|
| Glucose | 5.0% |
| Peptone | 1.0% |
| Yeast extract | 1.0% |
| Ammonium sulfate | 0.5% |
| Urea | 0.3% |
| Sodium chloride | 0.25% |
| Biotin | 50 μg/l |
| Uracil | 150 mg/l |
| Calcium carbonate | 2.0% |
| (pH 7.0) | |
| Production Medium | |
| Blackstrap molasses | 20% |
| Ammonium sulfate | 0.5% |
| Urea | 1.0% |
| Potassium dihydrogenphosphate | 0.05% |
| Dipotassium hydrogenphosphate | 0.05% |
| Magnesium sulfate | 0.05% |
| Uracil | 50 or 100 mg/l |
| Calcium carbonate | 2.0% |
| (pH 7.0) | |

TABLE 2

| Strain | Amount of Uracil added (mg/l) | Amount of Orotic Acid Accumulated (g/l) | |
|---|---|---|---|
| | | After 3 Days | After 5 Days |
| T-26 | 50 | 8.5 | 13.0 |
| | 100 | 8.2 | 12.5 |
| ATCC 14275 | 50 | 4.5 | 8.2 |
| | 100 | 4.0 | 7.5 |

EXAMPLE 2

The same culturing procedure as in Example 1 was repeated except that T-29 and T-30 were used as the seed strains in place of T-26. The results are shown in Table 3.

TABLE 3

| Strain | Amount of uracil added (mg/l) | Amount of Orotic Acid Accumulated (g/l) | |
|---|---|---|---|
| | | After 3 Days | After 5 Days |
| T-29 | 50 | 8.4 | 14.0 |
| T-30 | 50 | 11.2 | 14.5 |

EXAMPLE 3

One loopful each of the seed strains shown in Table 4 was inoculated into a 2 l-Erlenmeyer flask containing 200 ml of a seed culture medium having the composition shown in Example 1, and cultured at 30° C. for 24 hours The seed culture obtained was inoculated into a 5 l-jar fermentor containing 2 l of a production medium having the composition shown in Example 1, and cultured at 33° C. with agitation and aeration (rotation: 600 rpm, aeration: 1 vvm). Twenty-four hours after the start of the culturing, 500 ml of steilized 50% blackstrap molasses was added to the culture, and the culturing was continued. During the culturing, the pH of the culture was adjusted to 7.2 or more with concentrated aqueous ammonia. The results are shown in Table 4.

TABLE 4

| Strain | Amount of Uracil added (mg/l) | Amount of Orotic Acid Accumulated (g/l) | |
|---|---|---|---|
| | | After 70 hrs | After 84 hrs |
| T-26 | 60 | 37.0 | 50.3 |
| | 120 | 35.2 | 48.5 |
| T-29 | 60 | 42.8 | 53.2 |
| T-30 | 60 | 45.0 | 56.0 |
| ATCC 14275 | 60 | 17.5 | 28.5 |
| | 120 | 24.3 | 34.8 |

What is claimed is:

1. A process for producing orotic acid by fermentation which comprises culturing in a medium a microorganism which is capable of producing orotic acid and has resistance to a pyrimidine analogue or to both a pyrimidine analogue and a sulfa drug, until orotic acid is accumulated in the culture, and recovering orotic acid therefrom; said microorganism being Corynebacterium glutamicum T-26 (FERM BP-1487), Corynebacterium glutamicum T-29 (FERM BP-1488) or Corynebacterium glutamicum T-30 (FERM BP-1489).

2. A process according to claim 1, wherein said culturing is conducted at 25° to 37° C. and at pH 5 to 9 for 2 to 5 days.

* * * * *